(12) United States Patent
Dewey et al.

(10) Patent No.: US 6,462,084 B1
(45) Date of Patent: Oct. 8, 2002

(54) TREATMENT FOR OBSESSIVE-COMPULSIVE DISORDER (OCD) AND OCD-RELATED DISORDERS USING GVG

(75) Inventors: Stephen L. Dewey, Manorville, NY (US); Jonathan D. Brodie, Cos Cob, CT (US); Charles R. Ashby, Jr., Miller Place, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 09/853,392

(22) Filed: May 14, 2001

(51) Int. Cl.⁷ ............................................. A61K 31/195
(52) U.S. Cl. ..................................................... 514/561
(58) Field of Search ................. 514/561, 557, 514/620, 551, 455, 326, 629

(56) References Cited

U.S. PATENT DOCUMENTS

| | | |
|---|---|---|
| 4,761,429 A | 8/1988 | Blum et al. |
| 4,786,647 A | 11/1988 | Simplins et al. |
| 4,980,168 A | 12/1990 | Sahley |
| 5,189,064 A | 2/1993 | Blum et al. |
| 5,776,956 A | 7/1998 | Rolf |
| 5,792,796 A * | 8/1998 | Woodruff et al. ............ 514/561 |
| 6,117,855 A * | 9/2000 | Carlson et al. ................ 514/90 |

FOREIGN PATENT DOCUMENTS

| | | |
|---|---|---|
| EP | 543780 | 11/1992 |
| WO | WO 93/23383 * | 11/1993 |
| WO | WO 98/00130 | 1/1998 |
| WO | WO 99/21540 | 5/1999 |
| WO | WO 00/44374 | 8/2000 |
| WO | WO 00/50020 | 8/2000 |
| WO | WO 00/56301 * | 9/2000 |
| WO | WO 00/61140 | 10/2000 |

* cited by examiner

*Primary Examiner*—William R. A. Jarvis
(74) *Attorney, Agent, or Firm*—Margaret C. Bogosian

(57) ABSTRACT

The present invention relates to the use of gamma vinyl-GABA (GVG) to treat obsessive-compulsive disorder (OCD) and OCD-related disorders, and to reduce or eliminate behaviors associated with obsessive-compulsive disorder (OCD) and OCD-related disorders.

6 Claims, No Drawings

TREATMENT FOR OBSESSIVE-COMPULSIVE DISORDER (OCD) AND OCD-RELATED DISORDERS USING GVG

This invention was made with Government support under contract number DE-AC02-98CH10886, awarded by the U.S. Department of Energy. The Government has certain rights in the invention.

BACKGROUND OF THE INVENTION

This invention relates to the use of gamma vinyl-GABA and other GABAergic agents to reduce or eliminate the symptoms associated with obsessive-compulsive disorder (OCD) and OCD-related disorders. Obsessive-Compulsive Disorder effects a large portion of the population and can be disabling.

OCD has been linked to and can include one or more of the following OCD-related disorders: obsessive behavior, compulsive behavior, general anxiety disorder (GAD), pathological gambling, compulsive overeating, body dysmorphic disorder (BDD), hypochondriasis, pathologic grooming conditions (e.g. nail biting, skin picking, trichotillomania), kleptomania, pyromania, attention deficit hyperactivity disorder (AHDH), and any other impulse control disorder.

The fact that many individuals with OCD suffer from one or more OCD-related disorders may be due to the discovery that individuals who suffer from OCD or OCD-related disorders, demonstrate similar chemical imbalances in the brain and respond to similar drug therapies. For example, some research suggests that OCD involves problems with communication between the orbital cortex and the basal ganglia of the brain. These brain structures use the chemical messenger serotonin. Drugs that increase brain concentrations of serotonin have been used to treat OCD symptoms as well as symptoms of OCD-related disorders.

In the past, OCD and OCD-related disorders have been treated with serotonin reuptake inhibitors (SRIs) such as Clomipramine, Fluoxetine, Fluvoxamine, Paroxetine, Sertraline and Citalopram. These medications increase the concentration of serotonin in the brain.

Unfortunately, fewer than 20% of patents suffering from OCD and OCD-related disorders treated with SRIs have their OCD behavior eliminated. In addition, there are numerous side effects identified with SRIs which include: nervousness, insomnia, restlessness, nausea, diarrhea, weight gain and sexual problems.

Other research has suggested that the role of neurochemical systems in OCD and OCD-related disorders is unclear and that the serotonergic abnormalities in OCD patients may be a secondary phenomenon.

Several approaches to treating OCD and OCD-related disorders have been put forward, each based on a rather different framework. Overlap exists among these approaches, indicating that the neurobiology of OCD and OCD-related disorders is consolidated. The development of one effective treatment for OCD and all of the OCD-related disorders would be very beneficial. Accordingly, there is still a need in the treatment of OCD and OCD-related disorders to provide new methods which can reduce or eliminate the associated behaviors.

SUMMARY OF THE PRESENT INVENTION

The present invention, which addresses the needs of the prior art, provides methods for treating a mammal suffering from OCD and OCD-related disorders by administering to a mammal suffering from OCD and/or OCD-related disorders, an effective amount of a pharmaceutical composition including gamma vinylGABA (GVG).

In a preferred embodiment, the present invention provides a method for reducing or eliminating behaviors associated with OCD and OCD related disorders in a mammal suffering from OCD and/or OCD-related disorders. The method comprises administering to said mammal, an effective amount of a composition including gamma vinylGABA (GVG) or a pharmaceutically acceptable salt thereof, or an enantiomer or a racemic mixture thereof, wherein the effective amount reduces or eliminates behaviors associated with OCD and OCD-related disorders.

In another exemplary embodiment of the present invention, the method includes reducing or eliminating behaviors associated with OCD and OCD-related disorders in a mammal suffering from OCD. The method comprises administering to the mammal, an effective amount of a composition that increases central nervous system GABA levels, wherein the effective amount is sufficient to reduce or eliminate behaviors associated with OCD and OCD-related disorders.

As a result of the present invention, methods of reducing or eliminating behaviors associated with OCD and OCD-related disorders are provided which are based on pharmaceutical compositions which are highly effective in reducing or eliminating behaviors associated with OCD and OCD-related disorders in individuals suffering from OCD and OCD-related disorders.

The pharmaceutical compositions of the present invention provide treatments for OCD and OCD-related disorders that are very well tolerated and more efficacious than the current treatments available.

Other improvements over the prior art which are provided by the present invention will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION OF THE INVENTION

The present invention provides a highly effective method for treating OCD and OCD-related disorders, and reducing or eliminating behaviors associated with OCD and OCD-related disorders in mammals.

Effective treatment of OCD and OCD-related disorders includes temporary or permanent relief from the disorder or disorders that an affected mammal may suffer from.

OCD and OCD-related Disorders

As used herein, OCD is defined to include obsessive behavior and compulsive behavior. OCD-related disorders include, for example: general anxiety disorder (GAD), pathological or compulsive gambling disorder, compulsive eating, body dysmorphic disorder (BDD), hypochondriasis, pathologic grooming conditions (e.g. nail biting, skin picking, trichotillomania), kleptomania, pyromania, attention deficit hyperactivity disorder (ADHD) and other impulse control disorders.

Obsessive behavior is defined to include recurrent and persistent thoughts, impulses or images that occur over and over again and feel out of an individual's control. These thoughts cause marked anxiety and distress. Obsessive behavior can be accompanied by uncomfortable feelings, such as fear, disgust and doubt.

Compulsive behavior is defined to include acts or compulsions an individual with OCD performs over and over again, often according to certain rules. Compulsions are repetitive behaviors or mental acts that an individual feels driven to perform in response to an obsession.

Behaviors associated with Generalized Anxiety Disorder (GAD) are defined to include chronic and excessive worry about events that are unlikely to occur. Individuals with GAD can also experience a number of other physical and emotional difficulties, including trembling, muscular aches or soreness, restlessness, insomnia, sweating, abdominal upsets, dizziness, concentration problems, edginess and irritability.

Behaviors associated with Impulse Control Disorders include pathological and compulsive gambling, pyromania, kleptomania, trichotillomania, and intermittent explosive disorder. Individuals with these disorders can suffer from recurrent failure to resist impulsive behaviors that may be harmful to themselves or others.

Behaviors associated with pathological or compulsive gambling disorder are defined to include recurrent failure to resist gambling to such an extent that it leads to disruption of major life pursuits.

Behaviors associated with pyromania are defined to include recurrent failure to resist impulses to deliberately start fires, fascination with fire, its consequences and related activities (e.g. paraphernalia) and setting fires.

Behaviors associated with kleptomania are defined to include recurrent failure to resist impulsive stealing of objects.

Behaviors associated with intermittent explosive disorder are defined to include recurrent failure to resist impulsive aggressive destruction of property or assault of other persons far in excess of what might be considered appropriate with respect to any precipitating event.

Behaviors associated with compulsive overeating or binge eating are defined to include constant conscious or unconscious thoughts of food, and compulsive consumption of food in spite of the consequences.

Gamma Vinyl GABA (GVG)

The dopaminergic and opiodergic reward pathways of the brain are critical to survival since they provide the pleasure drives for eating, love and reproduction. These are called 'natural rewards' and involve the release of dopamine in the nucleus accumbens and frontal lobes of the brain. However, the same release of dopaminergic production of sensations and pleasures can be produced by 'unnatural rewards' such as compulsive behavior.

Dopaminergic (DA) neurons of the mesocorticolimbic dopamine system, whose cell bodies lie within the ventral tegmental area (VTA) and project primarily to the nucleus accumbens (NACC), appear to be involved in the reward center process. The present invention demonstrates that pharmacologic manipulation of gamma-aminobutyric acid A (GABA), a neurotransmitter in the brain, may effect DA levels in the NACC through modulation of VTA-DA neurons.

Gamma vinyl GABA (GVG) is a selective and irreversible inhibitor of GABA-transaminase (GABA-T) known to potentiate GABAergic inhibition. GVG also causes dependent and prolonged elevation of extracellular endogenous brain GABA levels.

GVG is $C_6H_{11}NO_2$ or 4-amino-5-hexanoic acid available as Vigabatrin® from Hoechst Marion Roussel and can be obtained from Marion Merell Dow of Cincinnati, Ohio.

GVG does not bind to any receptor or reuptake complex, but increases endogenous intracellular GABA levels by selectively and irreversibly inhibiting GABA-transaminase (GABA-T), the enzyme that normally catabolizes GABA.

As used herein GVG includes the racemic compound or mixture which contains equal amounts of S(+)-gamma-vinyl GABA, and R(−)-gamma vinyl GABA. This racemic compound of GVG is available as Vigabatrin® from Hoechst Marion Roussel and can be obtained from Marion Merell Dow of Cincinnati, Ohio.

GVG contains asymmetric carbon atoms and thus is capable of existing as enantiomers. The present invention embraces any enantiomeric form of GVG including the racemates or racemic mixture of GVG. In some cases there may be advantages, i.e. greater efficacy, to using a particular enantiomer when compared to the other enantiomer or the racemate or racemic mixture in the methods of the instant invention and such advantages can be readily determined by those skilled in the art.

For example, the enantiomer S(+)-gamma-vinyl GABA is more effective at increasing endogenous intracellular GABA levels than the enantiomer R(−)-gamma-vinyl GABA.

Different enantiomers may be synthesized from chiral starting materials, or the racemates may be resolved by conventional procedures which are well known in the art of chemistry such as chiral chromatography, fractional crystallization of diastereomeric salts, and the like.

In living mammals (in vivo), GVG or pharmaceutically acceptable salts thereof, can be administered systemically by the parenteral and enteral routes which also includes controlled release delivery systems. For example, GVG can easily be administered intravenously, or intraperitoneally (i.p.) which is a preferred route of delivery. Intravenous or intraperitoneal administration can be accomplished by mixing GVG in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide GVG or pharmaceutically acceptable salts thereof.

As used herein, pharmaceutically acceptable salts include those salt-forming acids and bases which do not substantially increase the toxicity of the compound. Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

An effective amount as used herein is that amount effective to achieve the specified result of treating the behaviors associated with OCD and OCD-related disorders and reducing or eliminating said behaviors. Preferably, GVG is administered in an amount which has little or no adverse effects.

Mammals include, for example, humans, baboons and other primates, as well as pet animals such as dogs and cats, laboratory animals such as rats and mice, and farm animals such as horses, sheep, and cows.

Based on the knowledge that OCD and OCD-related disorders may be caused by an increase in extracellular NACC-DA and the fact that GABA inhibits DA in the same nuclei, we have shown that GVG can reduce and/or eliminate the behaviors associated with OCD and OCD-related disorders.

It has unexpectedly been found that intake of GVG alters behavior, and especially behavior associated with OCD and OCD-related disorders. Rather than targeting the GABA receptor complex with a direct GABA agonist, this novel approach with GVG takes advantage of the prolonged effects of an irreversible enzyme inhibitor that raises endogenous GABA levels without the addictive liability associated with GABA agonists acting directly at the receptor itself.

Although GVG is used in the present examples, it will be understood by those skilled in the arts that other compositions can be used which are known to potentiate the GABAergic system or increase extracellular endogenous GABA levels in the CNS.

Other Compositions that Increase GABA Levels in the Central Nervous System

Compositions that increase extracellular GABA levels in the Central Nervous System (CNS) include drugs which enhance the production or release of GABA in the CNS. These drugs include, but are not limited to, gabapentin, valproic acid, progabide, gamma-hydroxybutyric acid, fengabine, cetylGABA, topiramate, tiagabine, acamprosate (homo calcium acetyltaurine) or a pharmaceutically acceptable salt thereof, or an enantiomer or a racemic mixture thereof.

The present invention embraces any enantiomeric form of gabapentin, valproic acid, progabide, gamma-hydroxybutyric acid, fengabine, cetylGABA, topiramate, tiagabine, or acamprosate, including the racemates or racemic mixtures thereof.

As previously stated, in some cases there may be advantages, i.e. greater efficacy, to using a particular enantiomer when compared to the other enantiomer or the racemate or racemic mixture in the methods of the instant invention and such advantages can be readily determined by those skilled in the art.

The present invention embraces compositions which include prodrugs of GABA or drugs which contain GABA as a moiety in its chemical structure. These prodrugs become pharmacologically active when metabolically, enzymatically or nonenzymatically biotransformed or cleaved into GABA in the CNS. An example of a prodrug of GABA is progabide, which upon crossing the blood brain barrier, increases endogenous CNS GABA levels.

As previously stated, Gamma vinyl GABA (GVG) is a selective and irreversible inhibitor of GABA-transaminase (GABA-T) known to potentiate GABAergic inhibition. Other compositions which inhibit GABA re-uptake in the CNS are also encompassed by the present invention. An example of a GABA re-uptake inhibitor is tiagabine.

The methods of the present invention are useful in potentiating the GABAergic system or increasing extracellular endogenous GABA levels in the CNS. As used herein, enhancing or increasing endogenous CNS GABA levels is defined to include increasing or up-regulating GABA levels substantially over normal levels in vivo, within a mammal. Preferably, endogenous CNS GABA levels are enhanced at least by from about 10% to about 600% over normal levels.

Dosages

An effective amount of GVG administered to a mammal includes an amount from about 10 mg/kg/day to about 100 mg/kg/day, preferably from about 25 mg/kg/day to about 80 mg.kg/day. In humans, the preferred range is from about 500 mg/kg/day to about 6 g/gday, more preferably from about 1 g/day to 4 g/day.

An effective amount of gabapentin administered to a mammal includes an amount from about 10 mg/kg/day to about 40/ mg/kg/day, preferably from about 15 mg/kg/day to about 30 mg/kg/day. In humans, the preferred range is from about 600 mg/day to about 3600 mg/day, more preferably from 900 mg/kg/day to about 2400 mg/day. Gabapentin is available as NEURONTIN® from Parke-Davis in the United States.

An effective amount of valproic acid administered to a mammal includes an amount from about 10 mg/kg/day to about 60 mg/kg/day, preferably from about 15 mg/kg/day to about 30 mg/kg/day. In humans, the preferred range is from about 750 mg/day to about 1750 mg/day. Valproic acid is available as DEPAKENE® from Abbott in the United States.

An effective amount of topiramate administered to a mammal includes an amount from about 5 mg/kg/day to about 80 mg/kg/day, preferably from about 5 mg/kg/day to about 15 mg/kg/day. In humans, the preferred range is from about 100 mg/day to about 1000 mg/day, more preferably from 200 mg/day to about 600 mg/day. Topiramate is available as TOPAMAX® from McNeil in the United States.

An effective amount of progabide administered to a mammal includes an amount from about 5 mg/kg/day to about 15 mg/kg/day. In humans, the preferred range is from about 1000 mg/day to about 3000 mg/day, more preferably form about 1500 mg/day to about 2500 mg/day. Progabide is available as GABRENE® from Synthelabo, France. The chemical formula of progabide is $C_{17}H_{16}N_2O_2$.

An effective amount of fengabine administered to a mammal includes an amount from about 5 mg/kg/day to about 75 mg/kg/day, preferably from about 15 mg/kg/day to about 50 mg/kg/day. In humans, the preferred range is from about 700 mg/day to about 4000 mg/day, more preferably from about 1000 mg/day to about 3000 mg/day. Fengabine is available as SL 79229 from Synthelabo, France. The chemical formula of fengabine is $C_{17}H_{17}C_{12}NO$.

An effective amount of gamma-hydroxybutyric acid administered to a mammal includes an amount from about 5 mg/kg/day to about 100 mg/kg/day, preferably from about 10 mg/kg/day to about 80 mg/kg/day. In humans, the preferred range is from about 700 mg/day to about 5000 mg/day, more preferably from 1000 mg/day to 4000 mg/day. Gamma-hydroxybutyric acid is available from Sigma Chemical. The chemical formula of gamma-hydroxybutyric acid is $C_4H_7O_3Na$.

An effective amount of tiagabine administered to a mammal includes an amount from about 2 mg/kg/day to about 40 mg/kg/day, preferably from about 5 mg/kg/day to about 20 mg/kg/day. In humans, the preferred amount is from about 16 mg/day to about 56 mg/day, more preferably from about 16 mg/day to about 32 mg/day. Tiagabine is available as GABATRIL® from Celphalon, U.S. The chemical formula of tiagabine is $C_{20}H_{25}NO_2S_2$.

An effective amount of acamprosate administered to the mammal is, preferably, an amount from about 25 mg/kg/day to about 400 mg/kg/day, preferably from about 50 mg/kg/day to about 200 mg/kg/day. In humans, the preferred range is from about 700 mg/day to about 3000 mg/day, more preferably from about 1000 mg/day to about 3000 mg/day. Acamprosate is available as CAMPRAL® from Merck-Lipha, France. The chemical name of acamprosate is calcium acetyl homotaurine.

What is claimed is:

1. A method for treating a mammal suffering from OCD or OCD-related disorders, comprising administering to said mammal a pharmaceutical composition that includes GVG or a pharmaceutically acceptable salt thereof, or an enantiomer or racemic mixture thereof, to effectively treat said disorders.

2. The method of claim 1, wherein said OCD-related disorder is selected from the group consisting essentially of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders.

3. The method of claim 1, wherein said mammal is a human and said composition contains GVG in an amount from about 500 mg/day to about 5000 mg/day.

4. A method for reducing or eliminating behaviors associated with OCD and OCD-related disorders in a mammal suffering from said disorders, comprising administering to said mammal a pharmaceutical composition that includes GVG or a pharmaceutically acceptable salt thereof, or an enantiomer or racemic mixture thereof, to reduce or eliminate said behaviors.

5. The method of claim 4, wherein said OCD-related disorder is selected from the group consisting essentially of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders.

6. The method of claim 4, wherein said mammal is a human and said composition contains GVG in an amount from about 500 mg/day to about 5000 mg/day.

* * * * *